US011582022B1

(12) United States Patent
Creek et al.

(10) Patent No.: US 11,582,022 B1
(45) Date of Patent: Feb. 14, 2023

(54) SECURE FILE TRANSFER SYSTEM AND METHOD

(71) Applicant: ADVANCED NEUROMODULATION SYSTEMS, INC., Plano, TX (US)

(72) Inventors: Greg Creek, Prosper, TX (US); James Thomas Nagle, Celina, TX (US); Jagatkumar Shah, Lake in the Hills, IL (US)

(73) Assignee: Advanced Neuromodulation Systems, Inc., Plano, TX (US)

(*) Notice: Subject to any disclaimer, the term of this patent is extended or adjusted under 35 U.S.C. 154(b) by 271 days.

(21) Appl. No.: 17/088,287

(22) Filed: Nov. 3, 2020

(51) Int. Cl.
*H04L 9/28* (2006.01)
*H04L 9/06* (2006.01)
*H04L 9/08* (2006.01)
*G16H 10/60* (2018.01)
*H04L 9/30* (2006.01)
*G16H 80/00* (2018.01)

(52) U.S. Cl.
CPC ........ *H04L 9/0631* (2013.01); *G16H 10/60* (2018.01); *G16H 80/00* (2018.01); *H04L 9/0637* (2013.01); *H04L 9/0643* (2013.01); *H04L 9/0825* (2013.01); *H04L 9/302* (2013.01)

(58) Field of Classification Search
CPC ... H04L 9/0631; H04L 9/0637; H04L 9/0643; H04L 9/0825; H04L 9/302; G16H 10/60; G16H 80/00

USPC ......... 713/165, 189, 191, 193, 175; 380/37, 380/282, 285
See application file for complete search history.

(56) References Cited

U.S. PATENT DOCUMENTS

| 8,762,712 | B1 * | 6/2014 | Kwan ............... H04L 9/0825 713/165 |
| 9,100,171 | B1 * | 8/2015 | Peterson ............ H04L 63/062 |
| 9,135,458 | B1 | 9/2015 | Hankins, Jr. et al. |
| 9,473,506 | B1 | 10/2016 | Hensley et al. |
| 10,332,107 | B2 | 6/2019 | Ferguson et al. |
| 2009/0037520 | A1 | 2/2009 | Loffredo |
| 2011/0291803 | A1 * | 12/2011 | Bajic ............... G08B 13/2462 340/10.1 |

* cited by examiner

*Primary Examiner* — Izunna Okeke
(74) *Attorney, Agent, or Firm* — Norton Rose Fulbright US LLP

(57) ABSTRACT

A scheme for securely transferring a patient data file to an intended recipient regardless of a transfer mode selected by a sender. Encryption system executing at the sender device is operative to encrypt each plaintext data line of a file, one by one, using a symmetric key and a starting IV that is incremented per each line, resulting in corresponding ciphertext lines added to an encrypted file. A hash is generated based on the encrypted file. An encrypted header containing the symmetric key, starting IV and the hash is generated using a public key of the recipient, which is appended to the encrypted file. The encrypted header and associated encrypted file are transmitted to the recipient in any manner. Upon receipt, the recipient decrypts the encrypted header using a private key to obtain the symmetric key, starting IV and the hash, which are used by the recipient to validate and decrypt the encrypted file on a line-by-line basis.

19 Claims, 9 Drawing Sheets

SECURE FILE TRANSFER SYSTEM AND METHOD

TECHNICAL FIELD

The present disclosure generally relates to secure file transfer systems and methods. More particularly, and not by way of any limitation, the present disclosure is directed to a system and method for facilitating secure file storage and transfer of files containing sensitive personal data, e.g., patient information including therapy information, regardless of a mode of transfer.

BACKGROUND

Implantable medical devices have changed how medical care is provided to patients having a variety of chronic illnesses and disorders. For example, implantable cardiac devices improve cardiac function in patients with heart disease by improving quality of life and reducing mortality rates. Respective types of implantable neurostimulators provide a reduction in pain for chronic pain patients and reduce motor difficulties in patients with Parkinson's disease and other movement disorders. A variety of other medical devices are proposed and are in development to treat other disorders in a wide range of patients.

Many implantable medical devices and other personal medical devices are programmed by a physician or other clinician to optimize the therapy provided by a respective device to an individual patient. Typically, the programming occurs using a variety of short-range communication links (e.g., inductive wireless telemetry, Bluetooth Low Energy (BLE), etc.) in an in-person or in-clinic setting.

Remote patient care is a healthcare delivery method that aims to use technology to provide patient health outside of a traditional clinical setting (e.g., in a doctor's office or a patient's home). It is widely expected that remote patient care may increase access to care and decrease healthcare delivery costs.

Regardless of whether remote care therapy or in-person therapy is administered, various pieces of sensitive patient data may be generated and logged during therapy. It is necessary that such data is safeguarded at all times, not the least because of the requirement of compliance with applicable health data privacy laws as well as the need to protect against data breaches by unscrupulous actors, among others. Further, when it is required that patient data be transmitted to an authorized entity for a legitimate purpose, it is of paramount importance that the data remains confidential and tamper-resistant during transfer.

Whereas advances in cryptographic methods with respect to maintaining confidentiality and integrity of files continue to grow apace, several lacunae remain, thereby requiring further innovation as will be set forth hereinbelow.

SUMMARY

Example embodiments of the present patent disclosure are directed to a system and method for facilitating secure transfer of a patient data file to an intended recipient regardless of a transfer mode selected by a sender. In one aspect, an encryption system executing at the sender device is operative to encrypt each plaintext data line of a file, one by one, using a symmetric cryptography system (SCS) key and a starting initialization vector (IV) that is incremented per each line, resulting in corresponding ciphertext lines that are added to an accumulative encrypted file. A cryptographic hash function is applied to accumulative encrypted file as the ciphertext lines are added iteratively to obtain a hash value. An encrypted header containing the SES key, starting IV and the hash is generated using a public key of the recipient, wherein the public key may be provisioned as part of an asymmetric cryptography system (ACS). The encrypted header is appended to the encrypted file, which may be transmitted to the recipient in any manner. Upon receipt, the recipient is operative to decrypt the encrypted header using a private key corresponding to the ACS public key in order to obtain the decrypted SCS key, decrypted starting IV and the decrypted hash. The recipient is further configured to calculate a hash of the encrypted file, which is compared against the decrypted hash to verify the integrity of the encrypted file. Responsive to determining that the calculated hash matches the decrypted hash received in the header, the recipient is operative to decrypt the encrypted file line by line, commencing with the SCS key and the decrypted starting IV, which is incremented per each ciphertext line. A corresponding set of plaintext data lines are accordingly obtained, which may be assembled into a complete patient data file by the recipient.

In one example embodiment, the SCS key used for sender-side encryption of a patient data file may be dynamically generated according to the Advanced Encryption Standard (AES), wherein the key may have a suitable length, e.g., a 128-bit key length conforming to AES-128, a 192-bit key length conforming to AES-192, and a 256-bit key length conforming to AES-256. In one example embodiment, the starting IV may be is dynamically generated and may comprise a k-bit length corresponding to the AES key. In one example embodiment, the plaintext lines of the patient data file may be iteratively encrypted using the AES in a cipher block chaining (CBC) mode in combination with an integer counter (CTR) mode, wherein the starting IV is incremented by 1 per each plaintext data line. In one example embodiment, a Secure Hash Algorithm (SHA) configured to provide a digest length of 256 bits (i.e., SHA-256) may applied to the encrypted file to obtain the hash value. In one example embodiment, a Rivest-Shamir-Adleman (RSA) public-private key cryptography system is applied at the sender as the ACS system to encrypt a header containing the AES key, starting IV and the SHA-256 hash. In a further embodiment, a header containing the message digest, the AES key and the starting IV may be padded to a length that matches a key modulus of the RSA public key for generating the encrypted header.

In some embodiments, a sender device may comprise at least one of a patient controller device, a clinician controller device, an implantable or a non-invasive personal medical device of a patient, which may be configured to execute example encryption methods disclosed herein. In some embodiments, accordingly, an example patient data file may be generated by a patient controller application executing at any one of the foregoing devices or apparatuses. In some embodiments, an intended recipient may comprise at least one of a public entity, a private entity, a healthcare provider, a governmental agency, a regulatory organization, and a medical insurance company, wherein an associated receiver device having a processor and executable program code may be configured to execute example decryption methods disclosed herein.

In still further aspects, one or more embodiments of a non-transitory computer-readable medium or distributed media containing computer-executable program instructions or code portions stored thereon are disclosed for performing example methods herein when executed by a processor entity of a patient controller device, a clinician controller device, an IMD, and/or a receiver device, etc., mutatis mutandis.

Additional/alternative features and variations of the embodiments as well as the advantages thereof will be apparent in view of the following description and accompanying Figures.

BRIEF DESCRIPTION OF THE DRAWINGS

Embodiments of the present disclosure are illustrated by way of example, and not by way of limitation, in the Figures of the accompanying drawings in which like references indicate similar elements. It should be noted that different references to "an" or "one" embodiment in this disclosure are not necessarily to the same embodiment, and such references may mean at least one. Further, when a particular feature, structure, or characteristic is described in connection with an embodiment, it is submitted that it is within the knowledge of one skilled in the art to effectuate such feature, structure, or characteristic in connection with other embodiments whether or not explicitly described.

The accompanying drawings are incorporated into and form a part of the specification to illustrate one or more exemplary embodiments of the present disclosure. Various advantages and features of the disclosure will be understood from the following Detailed Description taken in connection with the appended claims and with reference to the attached drawing Figures in which:

DETAILED DESCRIPTION

Figure 1:
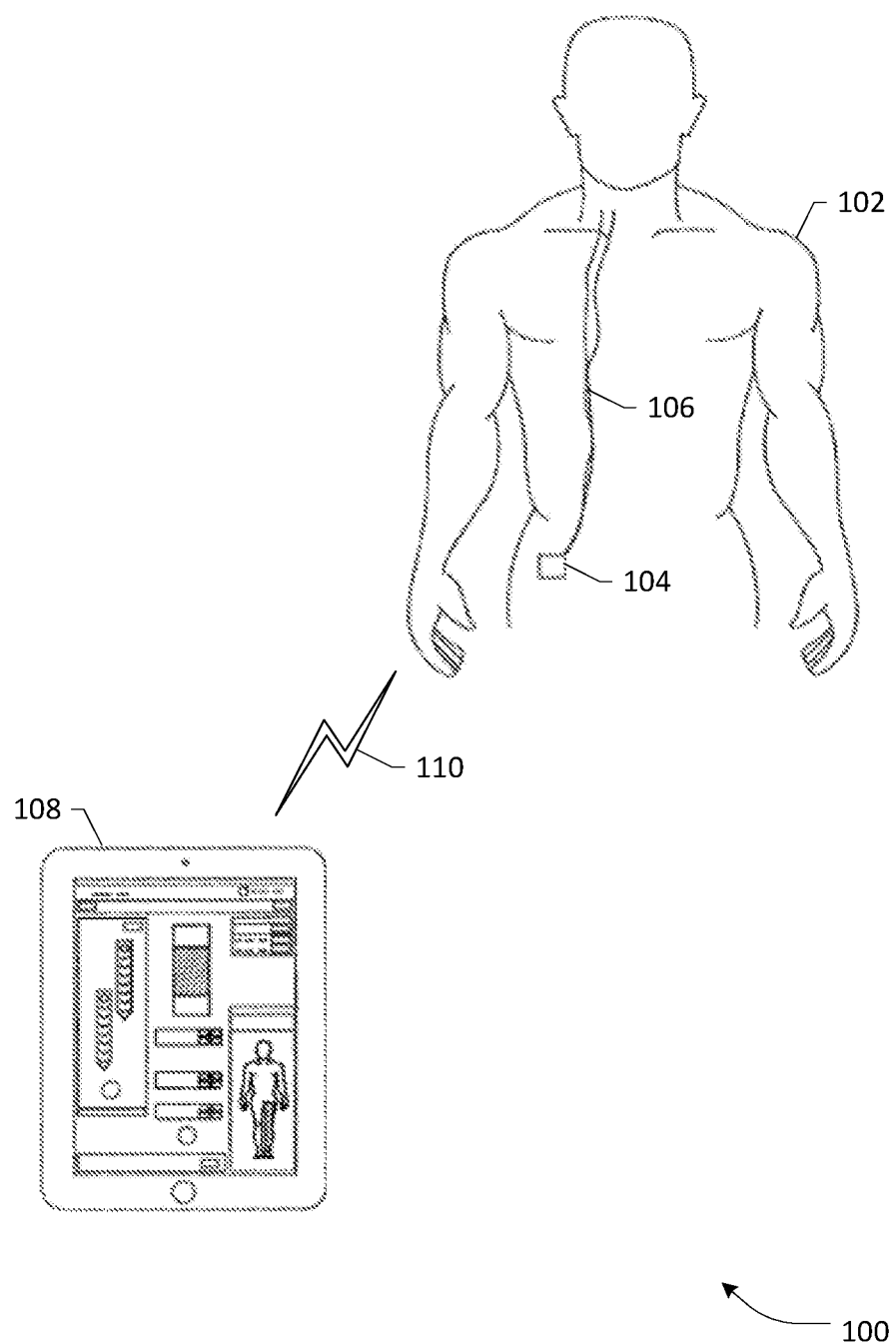
FIG. 1 depicts an example therapy system wherein a patient data file may be generated and securely packaged according to one or more embodiments of the present patent disclosure.

In the description herein for embodiments of the present disclosure, numerous specific details are provided, such as examples of circuits, devices, components and/or methods, to provide a thorough understanding of embodiments of the present disclosure. One skilled in the relevant art will recognize, however, that an embodiment of the disclosure can be practiced without one or more of the specific details, or with other apparatuses, systems, assemblies, methods, components, materials, parts, and/or the like set forth in reference to other embodiments herein. In other instances, well-known structures, materials, or operations are not specifically shown or described in detail to avoid obscuring aspects of embodiments of the present disclosure. Accordingly, it will be appreciated by one skilled in the art that the embodiments of the present disclosure may be practiced without such specific components. It should be further recognized that those of ordinary skill in the art, with the aid of the Detailed Description set forth herein and taking reference to the accompanying drawings, will be able to make and use one or more embodiments without undue experimentation.

Additionally, terms such as "coupled" and "connected," along with their derivatives, may be used in the following description, claims, or both. It should be understood that these terms are not necessarily intended as synonyms for each other. "Coupled" may be used to indicate that two or more elements, which may or may not be in direct physical or electrical contact with each other, co-operate or interact with each other. "Connected" may be used to indicate the establishment of communication, i.e., a communicative relationship, between two or more elements that are coupled with each other. Further, in one or more example embodiments set forth herein, generally speaking, an electrical element, component or module may be configured to perform a function if the element may be programmed for performing or otherwise structurally arranged to perform that function.

Some example embodiments described herein may relate to secure transfer of patient data files obtained in association with therapy applications, e.g., in-person therapy applications, telehealth applications as well as remote care therapy applications, that may be particularly set forth with respect to an implantable pulse generator (IPG) or neuromodulator for providing therapy to a desired area of a body or tissue based on a suitable stimulation therapy application, such as a spinal cord stimulation (SCS) system or other neuromodulation systems. However, it should be understood that example embodiments disclosed herein are not limited thereto, but have broad applicability, including but not limited to a variety of therapy settings involving different types of implantable devices such as neuromuscular stimulators and sensors, dorsal root ganglion (DRG) stimulators, deep brain stimulators, cochlear stimulators, retinal implanters, muscle stimulators, tissue stimulators, cardiac stimulators or pacemakers, gastric stimulators, and the like, as well as implantable drug delivery/infusion systems, implantable devices configured to effectuate real-time measurement/monitoring of one or more physiological functions of a patient's body (i.e., patient physiometry), including various implantable biomedical sensors and sensing systems. Further, whereas some example embodiments of therapy applications may involve implantable devices, additional and/or alternative embodiments may involve external personal devices, e.g., wearable biomedical devices, that may be configured to provide therapy to the patients analogous to the implantable devices. Accordingly, all such devices may be broadly referred to as "personal medical devices," "personal biomedical instrumentation," or terms of similar import, at least for purposes of some example embodiments of the present disclosure. Still further, the teachings of the present patent disclosure may also be practiced in a more generalized context involving data acquisition, storage, and file transmission (e.g., offline transmission), wherein confidentiality and integrity are desired regardless of a selected transfer modality while avoiding the need to use complex cryptographic key management schemes.

Referring to FIG. 1, depicted therein is an example therapy system wherein a patient data file comprising personal data, therapy information, etc., may be generated and securely packaged for purposes of effectuating offline transmission to an intended recipient according to one or more embodiments of the present patent disclosure. Example therapy system 100 is illustrative of a patient 102 having an implantable medical device (IMD) 104 and an external device 108 that may be controlled by the patient 102 and/or an authorized healthcare provider, e.g., a medical professional or technician, with respect to providing therapy to the patient 102. External device 108 may comprise commercial off-the-shelf (COTS) equipment such as a portable computer, smartphone, tablet, phablet, laptop, or the like, or a proprietary portable medical/healthcare device, which may be configured to execute a therapy application program or "app", wherein various types of communications relating to control, therapy/diagnostics, and/or device file management may be effectuated between one or more modules of the external device and IMD 104 for administering therapy and monitoring patient health data. Example IMD 104 may be implanted within the patient 102, e.g., proximate to the spinal cord or other tissue or organ depending on the therapy, wherein one or more leads 106 having one or more electrodes and/or sensors (not specifically shown in this FIG.) may be activated to provide therapy and/or obtain sense information. Additionally or alternatively, IMD 104 may have components that are external to the patient 102; for example, IMD 102 may be associated with an external pulse generator (EPG) that may also be configured to provide therapy and/or obtain therapy data.

In one arrangement, external device 108 may be configured to establish a local communication link, e.g., a bi-directional communication link 110, with IMD 104 for facilitating external device 108 to, inter alia, receive various pieces of information, e.g., therapy measurements, sensory data, personal data, logging data, etc., from IMD 104, and to program or send instructions to IMD 104. In one arrangement, the bi-directional communication link 110 may use any standard wireless protocol such as Bluetooth Low Energy (BLE), Bluetooth, Wireless USB, WiFi, and the like, as well as certain healthcare-specific communications services including, Medical Implant Communication Service, Wireless Medical Telemetry Service, Medical Device Radiocommunications Service, Medical Data Service, etc. In additional and/or alternative embodiments where remote care therapy is involved, external device 108 may be operative as a remote clinician device for providing therapy via a trusted communication link over a network (e.g., the Internet), wherein similar patient therapy information and data may be monitored and obtained. Details regarding remote care therapy for a patient may be found in one or more of the following common-owned co-pending patent application(s): (i) "SYSTEM, METHOD AND ARCHITECTURE FOR FACILITATING REMOTE PATIENT CARE", application Ser. No. 16/449,056, filed Jun. 21, 2019; (ii) "UI DESIGN FOR PATIENT AND CLINICIAN CONTROLLER DEVICES OPERATIVE IN A REMOTE CARE ARCHITECTURE", application Ser. No. 16/896,694, filed Jun. 9, 2020; (iii) "SYSTEM AND METHOD FOR MODULATING THERAPY IN A REMOTE CARE ARCHITECTURE", application Ser. No. 16/900,202, filed Jun. 12, 2020; and (iv) "DATA LABELING SYSTEM AND METHOD OPERATIVE WITH PATIENT AND CLINICIAN CONTROLLER DEVICES DISPOSED IN A REMOTYE CARE ARCHITECTURE", application Ser. No. 16/901,368, filed Jun. 15, 2020; each of which is incorporated by reference herein. Depending on whether a remote care therapy scenario is involved, external device 108 may therefore be located within a home of the patient/clinician, a hospital, an automobile, at an office of the patient or clinician, or at a remote location, and the like.

Regardless of the type of therapy involved and/or whether external device 108 is deployed as a device controlled by a clinician (e.g., operative as a clinician programmer device) or as a device controlled by a patient (e.g., operative as a patient controller device), various pieces of patient therapy information and personal data (collectively, "patient data") may be dynamically generated and/or logged during the operation of external device 108 in concert with IMD 104, which may need to be securely shared with an intended recipient entity for various purposes, e.g., regulatory compliance, audit of device performance and/or therapy efficacy, etc. As will be set forth further below, example external device 108 and/or IMD 104 may be configured to execute a tandem cryptography process or module for securely packaging the patent data as it is dynamically generated such that the encrypted patient data may be transmitted as a tamper-resistant file package using a variety of transfer modalities depending on a sending party's selection.

Figure 2:
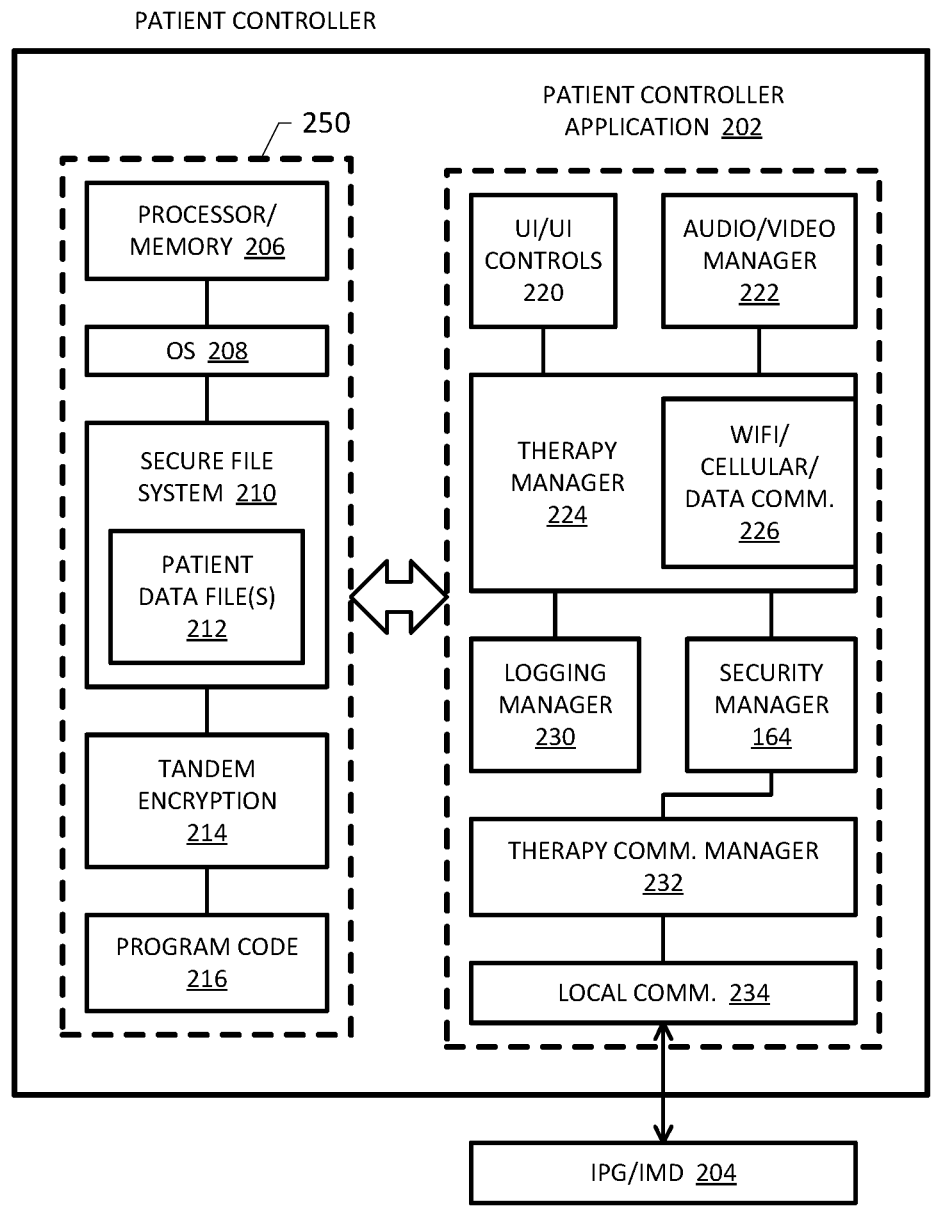
FIG. 2 depicts a block diagram of a patient controller device operative to securely package a patient data file according to an example embodiment of the present patent disclosure.

FIG. 2 depicts a block diagram of a patient controller device operative to securely package a patient data file according to an example embodiment of the present patent disclosure. Patient controller device 200 is a representative example of external device 108, wherein a patient controller application 202 may be configured to run in association with a suitable device hardware/software environment 250 effectuated by one or more processor and memory modules 206, one or more Operating System (OS) platforms 208, and one or more persistent memory modules 216 comprising program code or instructions for controlling overall operations of the device, inter alia. Example OS platforms may include embedded real-time OS systems, and may be selected from, without limitation, iOS, Android, Chrome OS, Blackberry OS, Ubuntu, Sailfish OS, Windows, Kai OS, eCos, LynxOS, QNX, RTLinux, Symbian OS, VxWorks, Windows CE, MontaVista Linux, and the like. In some embodiments, a secure file system 210 that can only be accessed by the patient controller application 202 may be provided, wherein one or more patient data files 212 may be stored in a packaged encrypted form according to the teachings herein. In some embodiments, patient controller application 202 may include a therapy manager 224 operative to facilitate remote and/or non-remote therapy applications and related communications using one or more communication interfaces, e.g., interface 234 with an implantable pulse generator or implantable medical device (IPG/IMD) 204 and network communications interface 236 with a network entity. A logging manager 230 associated with therapy manager 224 may be provided for logging data. A security manager 228 associated with therapy manager 224 may be provided for facilitating secure or trusted communications with a network entity in some embodiments. A therapy communication manager 232 may be provided for facilitating secure therapy communications between patient controller 200 and a clinician programmer (not shown in this FIG.). Therapy communication manager 232 may also be interfaced with local communication interface 234 to effectuate secure communications with the patient's IPG/IMD 204 using a suitable short-range communications technology or protocol as noted previously.

In still further arrangements, suitable software/firmware modules 220 may be provided as part of patient controller application 202 to effectuate appropriate user interfaces and controls, e.g., graphical user interfaces (GUIs), in association with an audio/video manager 222 for facilitating therapy/diagnostics control, file management, and/or other input/output (I/O) functions. Additionally, patient controller 200 may include a tandem encryption module 214 operative in association and/or otherwise integrated with patient controller application 202 for dynamically encrypting a patient data file on a line-by-line basis during runtime using a symmetric cryptography system (SCS), followed by the creation of an encrypted header using an asymmetric cryptography system (ACS), as will be set forth in detail further below.

Figure 3:
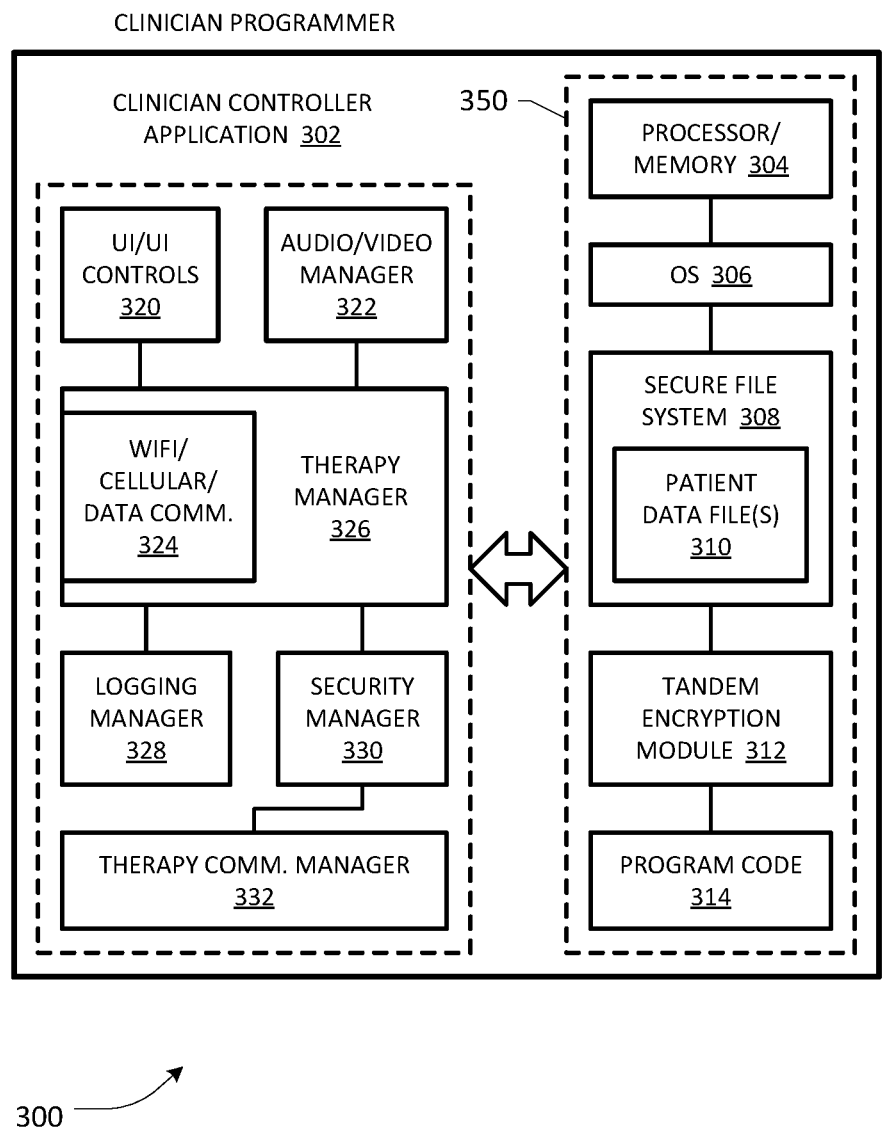
FIG. 3 depicts a block diagram of a clinician controller device operative to securely package a patient data file according to an example embodiment of the present patent disclosure.

FIG. 3 depicts a block diagram of a clinician controller device operative to securely package a patient data file according to an example embodiment of the present patent disclosure. Similar to patient controller device 200 of FIG. 2, clinician controller device 300, also referred to as a clinician programmer, is a representative example of external device 108 of FIG. 1 in some embodiments. A clinician controller application 302 may be configured to run in association with a suitable device hardware/software environment 350 effectuated by one or more processor and memory modules 304, one or more Operating System (OS) platforms 306, and one or more persistent memory modules 314 comprising program code or instructions for controlling overall operations of the device, inter alia. Example OS platforms may include embedded real-time OS systems, and may be selected from, without limitation, iOS, Android, Chrome OS, Blackberry OS, Ubuntu, Sailfish OS, Windows, Kai OS, eCos, LynxOS, QNX, RTLinux, Symbian OS, VxWorks, Windows CE, MontaVista Linux, and the like. Similar to example patient controller 200, a secure file system 308 may be provided in clinician programmer 300 that can only be accessed by the clinician controller application 302, wherein one or more patient data files 310 (e.g., corresponding to one or more patients) may be stored in a packaged encrypted form, respectively, in accordance with the teachings herein. In some embodiments, client controller application 302 may include a therapy manager 326 operative to facilitate remote and/or non-remote therapy applications and related communications using one or more communication interfaces, e.g., interface 324. For example, interface 324 may be configured to communicate with an IMD (not shown in this FIG.) using various short-range communication links with respect to in-person or in-clinic therapy according to some embodiments as previously noted. Likewise, example interface 324 may be configured to provide connectivity with wide-area networks for facilitating remote programming of an IMD in some scenarios. A logging manager 328 associated with therapy manager 324 may be provided for logging data for respective patients. A security manager 330 associated with therapy manager 324 may be provided for facilitating secure or trusted communications with a network entity in some embodiments. A therapy communication manager 332 may be provided for facilitating secure therapy communications between clinician controller 300 and a patient controller (not shown in this FIG.). Suitable software/firmware modules 320 may be provided as part of client controller application 302 to effectuate appropriate user interfaces and controls, e.g., graphical user interfaces (GUIs), in association with an audio/video manager 322 for facilitating therapy/diagnostics control, file management, and/or other input/output (I/O) functions. Further, clinician programmer 300 may include a tandem encryption module 312 similar to that of patient controller 200, wherein the tandem encryption module 312 is operative in association and/or otherwise integrated with clinician controller application 302 for dynamically encrypting a patient data file on a line-by-line basis during runtime using suitable cryptography systems in combination with hashing schemes as will be set forth in detail further below.

Figure 4:
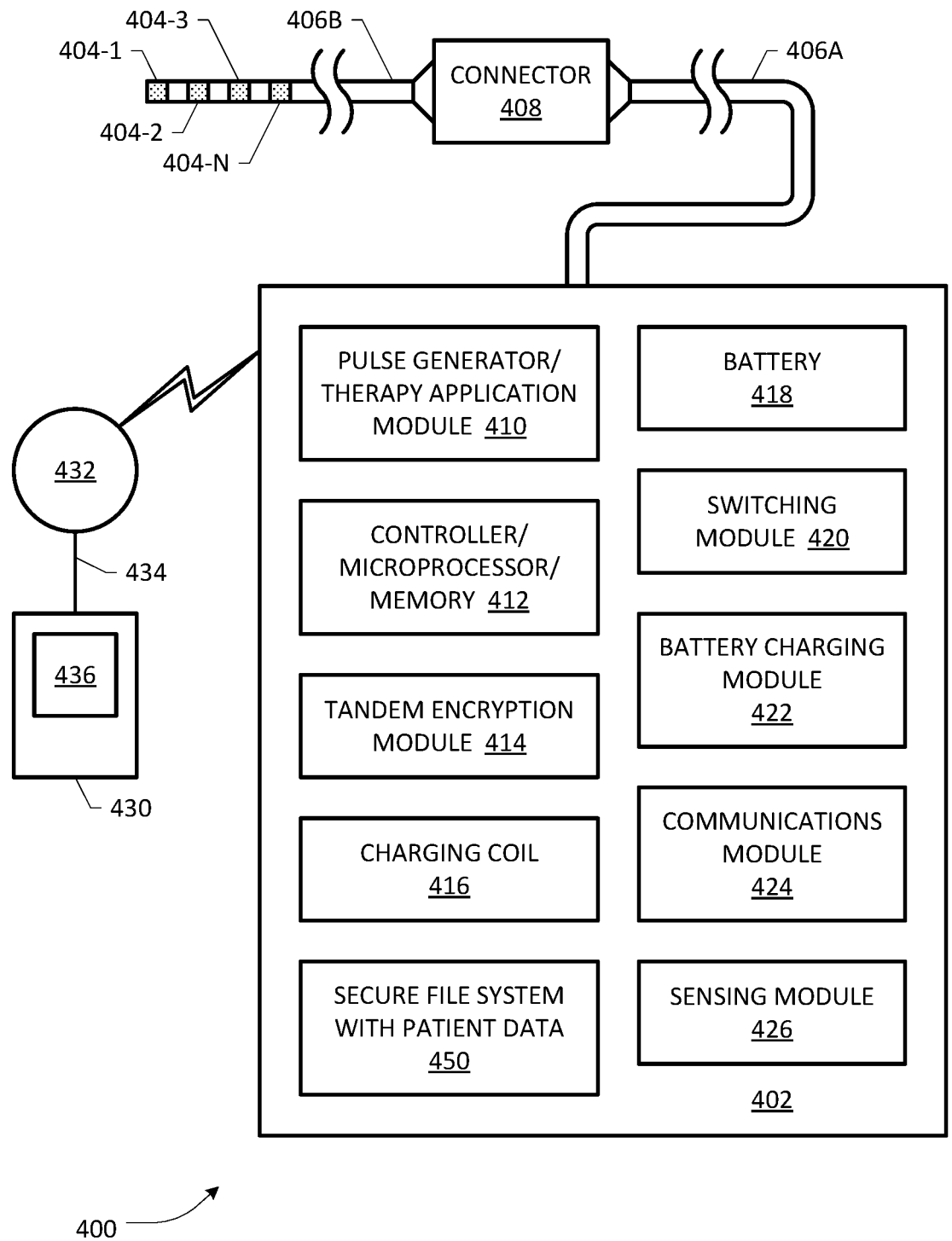
FIG. 4 depicts a block diagram of an implantable medical device (IMD) and associated system that may be configured for generating and securely packaging a patient data file according to an example embodiment of the present patent disclosure.

FIG. 4 depicts a block diagram of an IMD and associated external device disposed as a system that may be configured for generating and securely packaging a patient data file according to an example embodiment of the present patent disclosure. By way of illustration, system 400 may be adapted to stimulate spinal cord tissue, peripheral nerve tissue, deep brain tissue, DRG tissue, cortical tissue, cardiac tissue, digestive tissue, pelvic floor tissue, or any other suitable biological tissue of interest within a patient's body, as previously noted. System 400 includes an IMD 402 that is adapted to generate stimulation pulses according to known or heretofore known stimulation settings, programs, etc. In one example embodiment, IMD 402 may be implemented as having a metallic housing or can that encloses a controller/processing block and memory module 412, pulse generating circuitry with therapy application module 410, a charging coil 416, a battery or power source 418, a far-field and/or near field communication block or module 424, battery charging circuitry 422, switching circuitry 420, sensing circuitry 426, and the like. Controller/processor module 412 typically includes a microcontroller or other suitable processor for controlling the various other components of IMD 402. Software/firmware code may be stored in memory 412 of IMD 402, which may also be separately provided and/or integrated with other suitable application-specific storage components (not specifically shown in this FIG.) for execution by the microcontroller or processor 412 and/or other programmable logic blocks to control the various components of the device for purposes of an embodiment of the present patent disclosure. In one arrangement, IMD 402 may be coupled (via a "header" as is known in the art) to a lead system having a lead connector 408 for coupling a first component 406A emanating from IMD 402 with a second component 406B that includes a plurality of electrodes 404-1 to 404-N, which may be positioned proximate to the patient tissue. Although a single lead system 406A/406B is exemplified, it should be appreciated that an example lead system may include more than one lead, each having a respective number of electrodes for providing therapy according to configurable settings. For example, a therapy program may include one or more lead/electrode selection settings, one or more sets of stimulation parameters corresponding to different lead/electrode combinations, respectively, such as pulse amplitude, stimulation level, pulse width, pulse frequency or inter-pulse period, pulse repetition parameter (e.g., number of times for a given pulse to be repeated for respective stimulation sets or "stimsets" during the execution of a program), etc. Additional therapy settings data may comprise electrode configuration data for delivery of electrical pulses (e.g., as cathodic nodes, anodic nodes, or configured as inactive nodes, etc.), stimulation pattern identification (e.g., tonic stimulation, burst stimulation, noise stimulation, biphasic stimulation, monophasic stimulation, and/or the like), etc. Still further, therapy programming data may be accompanied with respective metadata, which may include data that identifies the physician or clinician that created or programmed the settings data. In some embodiments, the metadata may include an identifier of the clinician programmer device that was used to create the settings data, the date of creation, the data of last modification, the physical location where programming occurred, and/or any other relevant data or indicia.

In some embodiments, IMD 402 may include a secure file system 450 for logging patient data as it is generated. In some embodiments, IMD 402 may further include a tandem encryption module 414 operative for securely storing the patient data. In some embodiments, IMD 402 may be configured to coordinate with an external device 430 for facilitating secure transfer of the patient data as will be set forth below.

As noted previously, external device 430 may be deployed for use with IMD 402 for therapy application, management and monitoring purposes, e.g., either as a patient controller device or a clinician programmer device. Generally, external device 430 may be implemented to charge/recharge the battery 418 of IPG/IMD 402 (although a separate recharging device could alternatively be employed), to access memory 414 and/or secure file system 450, and/or to program or reprogram IPG 402 with respect to one or more stimulation set parameters including pulsing specifications while implanted within the patient. In alternative embodiments, however, separate programmer devices may be employed for charging and/or programming the IMD device 402 device and/or any programmable components thereof. Software stored within a non-transitory memory of the external device 430 may be executed by a processor to control the various operations of the external device 430, including facilitating encryption of patient data logged in or by IMD 402 and extracted therefrom. A connector or "wand" 434 may be electrically coupled to the external device 430 through suitable electrical connectors (not specifically shown), which may be electrically connected to a telemetry component 432 (e.g., inductor coil, RF transceiver, etc.) at the distal end of wand 434 through respective communication links that allow bi-directional communication with IMD 402.

In general operation, a user (e.g., a doctor, a medical technician, or the patient) may initiate communication with IMD 402 by placing the wand 434 proximate to the patient's body containing the IMD. Preferably, the placement of the wand 434 allows the telemetry system to be aligned with the far-field and/or near field communication circuitry 424 of IMD 402. External device 430 preferably provides one or more user interfaces 436 (e.g., touch screen, keyboard, mouse, buttons, scroll wheels or rollers, or the like), allowing the user to operate IMD 402. External device 430 may be controlled by the user through the user interface 436, allowing the user to interact with IMD 402, whereby operations involving therapy application/programming, coordination of patient data security including encryption, etc. may be effectuated.

Depending on IMD implementation and/or applicable regulatory regimes, information relating to therapy and diagnostics, including therapy settings data as well as any information relating to or arising out of patient/clinician interactions with the IMD, may be individualized, logged, and/or identified using a variety of personal information belonging to the patient and/or the clinician. For example, information such as device identifiers and serial numbers, patient/clinician names, geographical identifiers, birth dates, phone numbers, email addresses, medical record numbers, Uniform Resource Locators (URLs), IP addresses, Social Security Numbers, bank account numbers, driver's license numbers, credit card numbers, gender and address information, demographic data, biometric identifiers (e.g., finger, retinal and voice prints), photographic images, and/or other unique identifiers or indicia, etc., may be associated with time-stamped therapy information while generating one or more log files with respect to therapy. As such, therapeutic and/or diagnostic information generated during the lifecycle of an IMD that is associated with personal information linked to specific individuals may be deemed as electronic medical records containing protected health information (PHI) under certain healthcare-related regulatory schemes (e.g., the US Health Insurance Portability and Accountability Act or HIPAA). Further, such information may also be subject to other data protection and privacy regimes and guidelines, such as, e.g., the EU-based General Data Protection Regulation (GDPR), the National Institute of Standards and Technology (NIST) Special Publication 800-122 in the US, etc. Information monitored, generated and/or otherwise obtained in a therapy environment (e.g., remote or otherwise) therefore not only needs to be safeguarded during storage but it also becomes imperative that such information be protected during transfer to an authorized entity regardless of the mode or method of transfer selected by a sender, e.g., a patient or a clinician.

Accordingly, it is clear that secure transfer of files using offline methods (that is, extracting the file from its original source, and using methods independent of that original source to transfer the file to an intended recipient) must provide end-to-end confidentiality and integrity with respect to the files being moved. However, reliance on file transfer methods such as secure web transfer services or file repositories that are mutually accessible by both the sender and recipient leave a gap in the file's protection in the time between its extraction from the original source and delivery to the selected transfer method. Additionally, there exist vulnerabilities in third-party transfer methods that may also render the file subject to attack, e.g., tampering, during the transfer process itself. In order to ensure end-to-end protection, accordingly, the security properties of confidentiality and integrity must be applied to the file, e.g., a patient data file, by the source of the file itself prior to its extraction in a way that can be verified by the recipient of the file. Whereas cryptographic methods may be used to accomplish these goals, in an environment in which there is no direct connectivity between the original source of the file and the end recipient of the file (e.g., offline transfer), typical implementations such as the use of Transport Layer Security (TLS) with mutual authentication cannot be used. The challenge in such an environment is how to apply cryptography in an innovative way that does not introduce key management methods that are too complex, rely on hard-coded symmetric keys, or introduce errors in cryptographic methods such as those identified by the MITRE Corporation in the Common Weakness Enumeration (CWE) category system for software weaknesses and vulnerabilities.

Broadly, embodiments herein provide a tandem encryption scheme that involves a combination of symmetric and asymmetric cryptography in a way that provides confidentiality, integrity, and authenticity while ensuring scalability, minimizing the logistical burden for key management, and avoiding the pitfalls of hard-coded symmetric keys. In some example embodiments, the source (or the sending device) of a file may be configured to apply a symmetric cryptography system such as the Advanced Encryption Standard (AES) to provide symmetric encryption of the file by encrypting each line of the file before the line is written to the source device's file system. It should be appreciated that this aspect of the disclosed tandem encryption scheme according to an example embodiment advantageously prevents a plaintext version of the file from ever existing in the file system and minimizes exposure of plaintext data in volatile memory, since there is never a large set of plaintext in volatile memory that could be dumped or exploited. In one arrangement, the AES key and a starting initialization vector (IV) may be dynamically generated by the file source, wherein a combination of the cipher block chaining (CBC) and counter (CTR) modes of AES may be used to ensure maximum entropy between each line of the file for encryption by preventing re-use of an IV. Once the file is encrypted, a checksum or a cryptographic hash function may be applied to the ciphertext file to generate a digest or hash that is operative as an integrity check value. The AES key, AES IV, and file hash are placed into a header that may be encrypted using a public key of the recipient in an asymmetric cryptography system (ACS) such as the Rivest-Shamir-Adleman (RSA) scheme. In some embodiments, the encrypted header may be appended to the ciphertext file, which may be extracted and transferred to the intended recipient any arbitrary method of the sender's choice. Because the intended recipient is in possession of the RSA private key that corresponds to the public key, a reverse tandem process may be used to decrypt the header and use the retrieved hash to verify against a calculated hash in order to check the integrity of the encrypted file. Accordingly, once the recipient receives or otherwise obtains the encrypted file package regardless of the transfer modality, the recipient device or a suitable program executing thereon may be configured to use the RSA private key to decrypt the header, whereupon a hash value of the encrypted file may be calculated and compared against the value contained in the header to ensure that the file has not been modified or otherwise tampered with in route. After the file integrity has been verified, the recipient can use the AES key and associated starting IV to decrypt the file following the same method of the combined CBC and CTR modes. To facilitate concordance and coordination between the sender and the recipient processes, an out of band mechanism may be provided in some example embodiments such that the recipient is aware of the AES modes, IV incrementation and hashing schemes used at the sender side. Relatedly, suitable program logic may be provided as part of respective application software executing at the sender and recipient devices according to some embodiments in order to facilitate a priori negotiation with respect to an agreed-upon sequence of encryption schemes, modes, etc.

Skilled artisans will recognize upon reference hereto that AES encryption of the file provides confidentiality, cryptographic hashing provides integrity, and RSA encryption of the AES key and IV ensures that only the intended recipient can decrypt the file, avoiding the need to use complex key management schemes to protect pre-generated AES keys. Additional details regarding the foregoing embodiments are set forth immediately hereinbelow.

Figure 5:
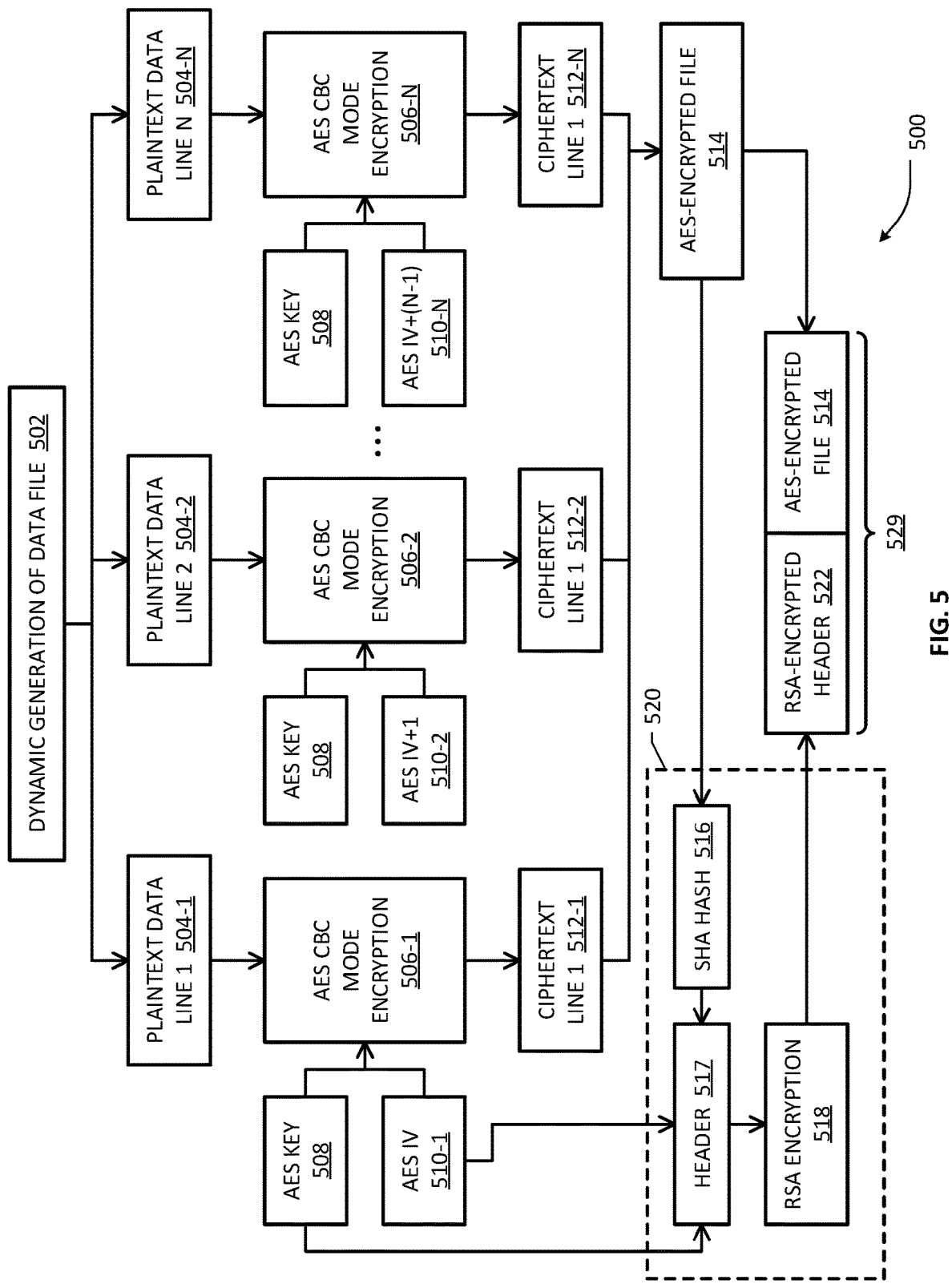
FIG. 5 depicts a functional block diagram of an encryption system operative at a sender device according to an example embodiment of the present patent disclosure.

FIG. 5 depicts a functional block diagram of a tandem encryption system 500 operative at a sender device according to an example embodiment of the present patent disclosure. A file source or program, which may be operative as part of executable code on a patient controller, clinician programmer and/or an IMD, may be configured to generate a patient data file, as exemplified at block 502. In an example embodiment, the source of the file may use the AES algorithm to provide symmetric encryption of the file on a line-by-line basis. At runtime, the source of the file dynamically generates a symmetric AES key 508 having a suitable length (e.g., 128-bit, 192-bit, or 256-bit, or any other length) using, e.g., random methods such as generating a byte array composed of randomly-generated numbers. In one arrangement, AES in the CBC mode uses an IV to ensure entropy, wherein a starting IV 510-1 having a suitable length corresponding to the AES encryption key 508 (e.g., a 128-bit IV) may be dynamically generated at runtime. The lines to be written to the file are encrypted individually as they are created, as exemplified by plaintext data lines 504-1 to 504-N, using the AES key 508 and an IV incrementation scheme. As noted previously, this arrangement is operative to prevent a plaintext version of the sensitive contents of the patient data file from ever existing in non-volatile memory of the sender device. To prevent re-use of the IV from line to line, the source of the file may be configured to implement the feature of IV incrementing from the CTR mode of AES encryption, wherein for each line added to the file, the IV may be incremented by a value, e.g., 1, line by line, thereby ensuring that the IV used for each round of AES-CBC encryption is unique without having to generate a unique IV for each line. As exemplified in FIG. 5, blocks 506-1 to 506-N of encryption system 500 illustrate the line-by-line AES encryption scheme, wherein block 506-1 is operative to apply AES key 508 and starting IV 510-1 to encrypt plaintext data line 1 504-1, block 506-2 is operative to apply AES key 508 and first-incremented IV 510-2 to encrypt plaintext data line 2 504-2, and so on, up to block 506-N operating to apply AES key 508 and $(N-1)^{th}$-incremented IV 510-N to encrypt plaintext data line N 504-N. Accordingly, a corresponding plurality of ciphertext lines 512-1 to 512-N are obtained line-by-line as each plaintext line is generated during runtime, whereby each corresponding ciphertext line is added into an accumulative encrypted file 514. It will be recognized that each plaintext line may be operated upon in blocks of suitable sizes, and there may be padding in a final plaintext block of a data line in some instances, depending on the AES implementation.

In one arrangement, after the accumulative encrypted file 514 is closed and completed, a header 517 may be created, wherein the AES key 508, starting IV 510-1 and a hash value 516 of the encrypted file 514 may be are placed. In one arrangement, a Secure Hash Algorithm (SHA) configured to provide a digest length of 256 bits may be used, although skilled artisans will recognize that other digest lengths and/or cryptographic hash functions may be utilized. In one arrangement, the header 517 may be padded to an appropriate length to match the key modulus of the RSA public key (e.g., 4096-bit) associated with the intended recipient in order to prevent discernable patterns in the ciphertext version of the header due to large amounts of zero padding, thereby rendering the scheme less vulnerable to cryptanalytic attacks. For example, Optimal Asymmetric Encryption Padding (OAEP) may be used for padding to match a 4096-bit key length. Header 517, which may be padded or unpadded depending on implementation, is then encrypted with the RSA public key encryption 518 to generate an encrypted header 522, which may be appended to or otherwise associated with the encrypted file 514 to obtain a secure data package 529. The RSA public key may be distributed out-of-band or may be pre-placed or otherwise stored in the sending device, depending on implementation. As such, the RSA public key is not sensitive and may therefore be provided to the sender in a number of ways pursuant to a suitable public key infrastructure (PKI) implementation.

Skilled artisans will recognize that AES encryption, hashing and creation of encrypted header may be performed iteratively as each line of a patient data file is generated. In such a scenario, each time the accumulated encrypted file 514 is augmented with an encrypted line, the hash value may be updated and placed into header 517, which is then encrypted to generate an updated encrypted header 522. In FIG. 5, an iterative updating process 520 is exemplary of such repetitive operations, which may be executed as the patient data lines are generated under programmatic control processes.

After the encrypted header 522 is generated and associated with the encrypted patient data file 514, secure data package 529 containing the header 522 and associated file 514 may be retrieved or extracted, which may be transferred to the recipient(s) in a variety of modes, e.g., as email attachments, via File Transfer Protocol (FTP) service, or by way of storing on physical media and shipping such media, etc. It will be recognized that the encrypted header 522 and associated file 514 may also be transmitted via separate modes and/or asynchronously in some arrangements as long as a matching mechanism is provided to match the encrypted header 522 with the correct encrypted file 522 at or by the recipient.

Figure 6:
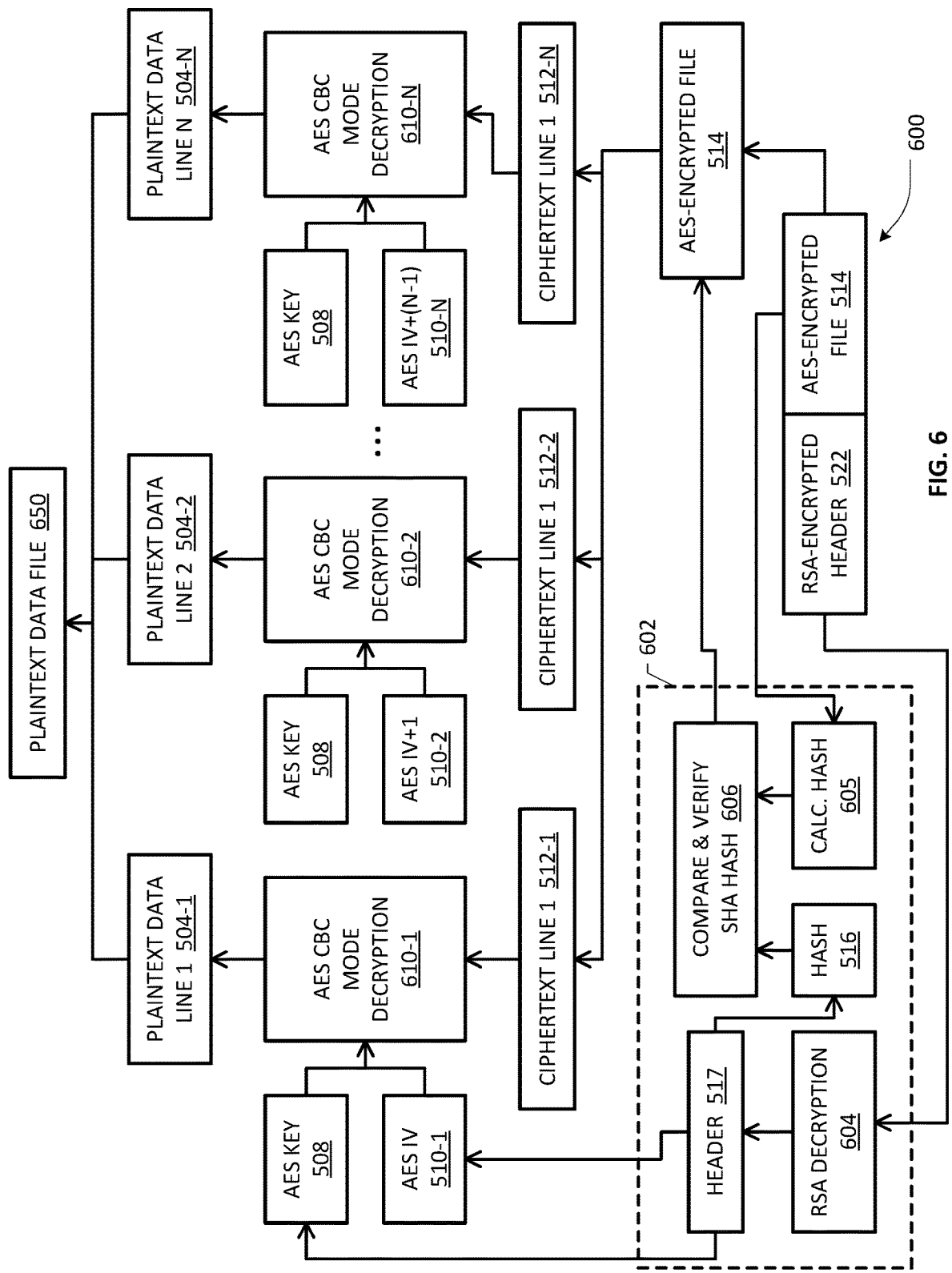
FIG. 6 depicts a functional block diagram of a decryption system operative at a recipient device according to an example embodiment of the present patent disclosure.

FIG. 6 depicts a functional block diagram of a tandem decryption system 600 operative at a recipient device according to an example embodiment of the present patent disclosure. After receiving a secure data package 529 including encrypted header 522 and associated encrypted file 514 via one or more transfer modes, the intended recipient, having possession of the RSA private key that corresponds to the public key used to encrypt the file header 517, is operative to decrypt the encrypted file header 522 using the private key of the RSA decryption scheme 604. The decrypted header 517 yields the file hash 516, and the AES key 508 and starting IV 510-1. It should be appreciated that whereas sender-side encryption/hashing processes 520 are performed iteratively for a number times depending on the number of plaintext data lines generated, receiver-side operations 602 are performed one time only to decrypt the contents of the received encrypted header 522. Thereafter, the recipient device is operative to independently calculate a SHA-256 hash of the encrypted file 514 to obtain a calculated hash 605, which is compared against the hash value 516 that was contained in the decrypted header 517, as set forth at hash compare and verify block 606, thereby ensuring that the encrypted file 514 has not been modified or otherwise tampered with in route.

Once the file integrity has been verified, the recipient uses the AES key 508 and IV 510-1 obtained from the decrypted header 517 in order to decrypt the encrypted file 514 line-by-line in a manner analogous to the encryption scheme 500. Each ciphertext line 512-1 to 512-N is decrypted using AES in the CBC mode, while the transition between lines in the file is treated the same as AES in the CTR mode, wherein the IV is incremented by a value, e.g., 1, for decrypting the corresponding line, thereby ensuring that the IV used for each round of AES-CBC decryption is the same as that used for encryption without having to generate a unique IV for each line. As exemplified in FIG. 6, decryption system 600 includes blocks 610-1 to 610-N operative to effectuate the line-by-line AES decryption scheme, wherein block 610-1 is operative to apply AES key 508 and starting IV 510-1 to decrypt ciphertext line 1 512-1, block 610-2 is operative to apply AES key 508 and first-incremented IV 510-2 to decrypt ciphertext line 2 512-2, and so on, up to block 610-N operating to apply AES key 508 and $(N-1)^{th}$-incremented IV 510-N to decrypt ciphertext line N 512-N. Accordingly, a corresponding plurality of plaintext data lines 504-1 to 504-N are generated line-by-line, which may be combined or otherwise reconstituted to be recovered as a full patient data file in plaintext form 650.

Figure 7:
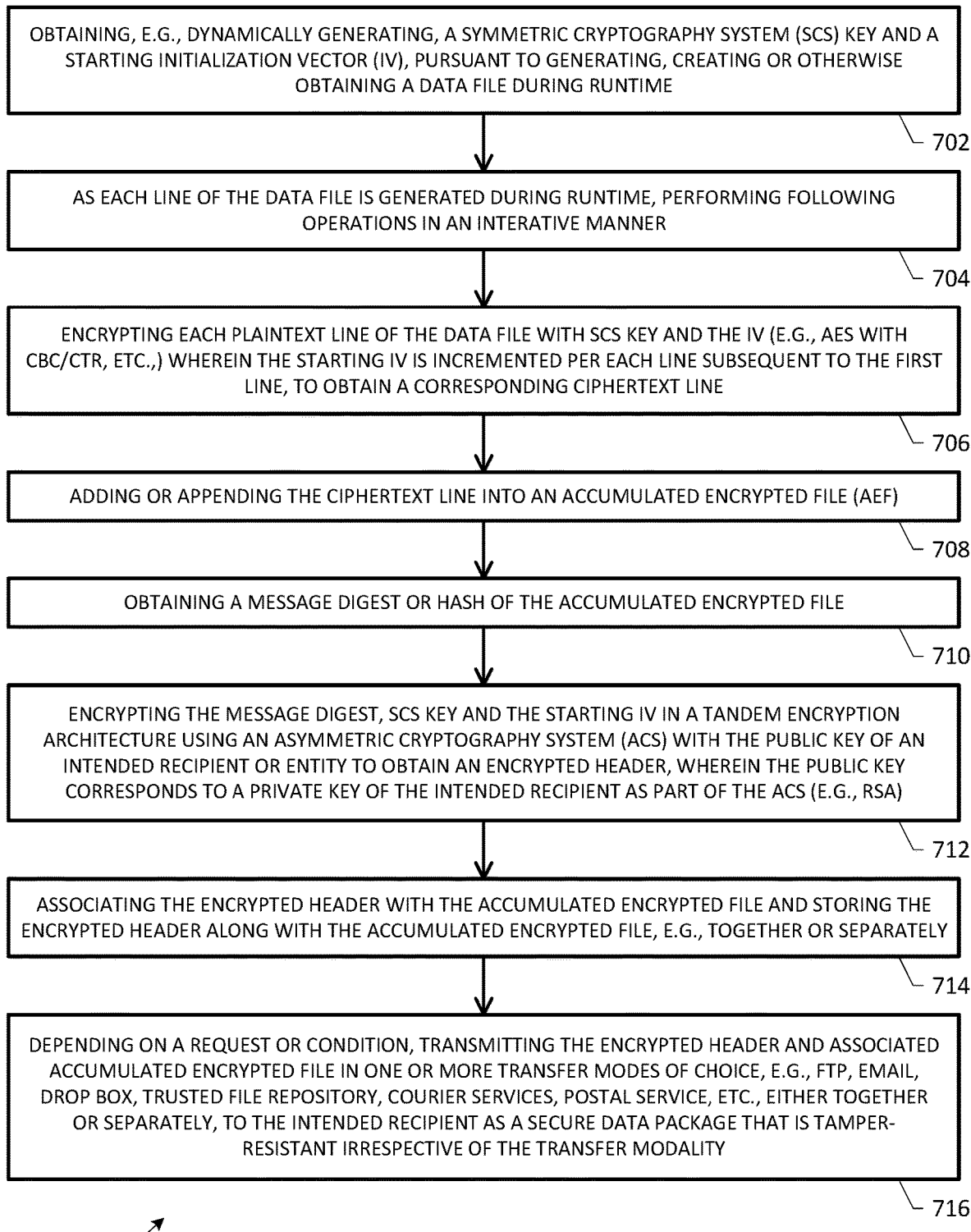
FIGS. 7 and 8 depict flowcharts illustrative of blocks, steps and/or acts that may be (re)combined in one or more arrangements with or without additional flowcharts of the present disclosure for facilitating secure transfer of a patient data file according to some embodiments.
Figure 8:
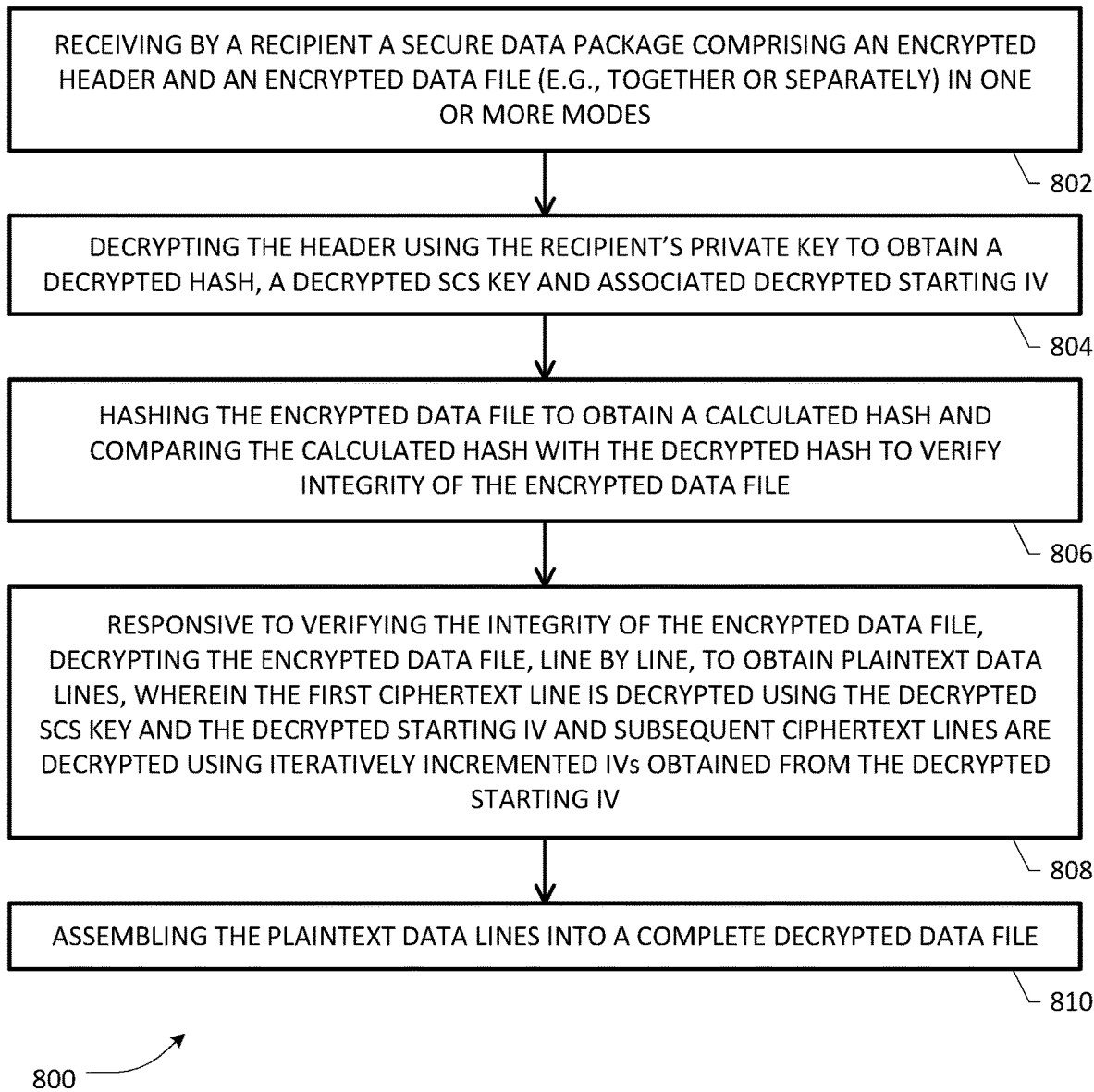

FIGS. 7 and 8 depict flowcharts illustrative of blocks, steps and/or acts that may be (re)combined in one or more arrangements with or without additional flowcharts of the present disclosure for facilitating secure transfer of a patient data file according to the foregoing embodiments. Process flow 700 of FIG. 7 is illustrative of a tandem encryption process at a sender in one arrangement. At block 702, a symmetric cryptography system (SCS) key and a starting IV may be obtained, e.g., dynamically generated, pursuant to generating, creating or otherwise obtaining a data file during runtime. At block 704, a repetitive process may be commenced as each line of the data file is generated during runtime, wherein a plurality of operations may be performed in an iterative manner. At bock 706, each plaintext line of the data file is encrypted with the SCS key and the IV (e.g., AES with CBC/CTR, etc.) wherein the starting IV is incremented per each line subsequent to the first line, in order to obtain a corresponding ciphertext line. At block 708, the ciphertext line is added or appended into an accumulated or accumulative encrypted file (AEF). At block 710, a message digest or hash of the accumulated encrypted file may be obtained. Thereafter, the message digest, SCS key and the starting IV may be encrypted in a tandem encryption architecture using an asymmetric cryptography system (ACS) with the public key of an intended recipient or entity to obtain an encrypted header, wherein the public key is corresponds to a private key of the intended recipient as part of the ACS (e.g., RSA scheme), as set forth at block 712. At block 714, the encrypted header is associated with the accumulated encrypted file. As noted previously, the encrypted header and the accumulated encrypted file may be stored at the sender device either together or separately. The foregoing operations may take place in a repetitive manner as long as the accumulated encrypted file remains open and operative to receive ciphertext lines as they are generated in one embodiment. Further, an accumulated encrypted file may be open as long as needed or may be closed periodically or otherwise, which may be responsive to a determination that the accumulative encrypted file is ready and/or a request for secure transfer is obtained. Depending on a request or a condition, accordingly, the encrypted header and associated accumulated encrypted file may be transmitted in one or more transfer modes of choice, e.g., FTP, email, drop box, trusted file repository, courier services, postal service, etc., either together or separately, to the intended recipient as a secure data package that is tamper-resistant irrespective of the transfer modality (block 716).

Process flow 800 of FIG. 8 is illustrative of a tandem decryption process at a recipient in one arrangement. At block 802, a secure data package comprising an encrypted header and an encrypted data file (i.e., a ciphertext file) may be received by a recipient in one or modes of transfer (e.g., together or separately). If the encrypted header and the encrypted data file corresponding thereto are received separately and/or asynchronously, example process flow 800 may involve a matching mechanism to ascertain that the received encrypted header and encrypted data file are matched correctly for subsequent operations. At block 804, the received encrypted header is decrypted using the recipient's private key to obtain a decrypted hash, a decrypted SCS key and associated decrypted starting IV. At block 806, the encrypted data file is hashed to obtain a calculated hash or digest, which may be compared with the decrypted hash to verify the integrity of the encrypted data file. At block 808, responsive to verifying the integrity of the encrypted data file, the encrypted data file may be decrypted, line by line, to obtain plaintext data lines, wherein the first ciphertext line is decrypted using the decrypted SCS key and the decrypted starting IV and subsequent ciphertext lines are decrypted using iteratively incremented IVs obtained from the decrypted starting IV. At block 810, the plaintext data lines may be assembled into a complete decrypted data file.

Figure 9:
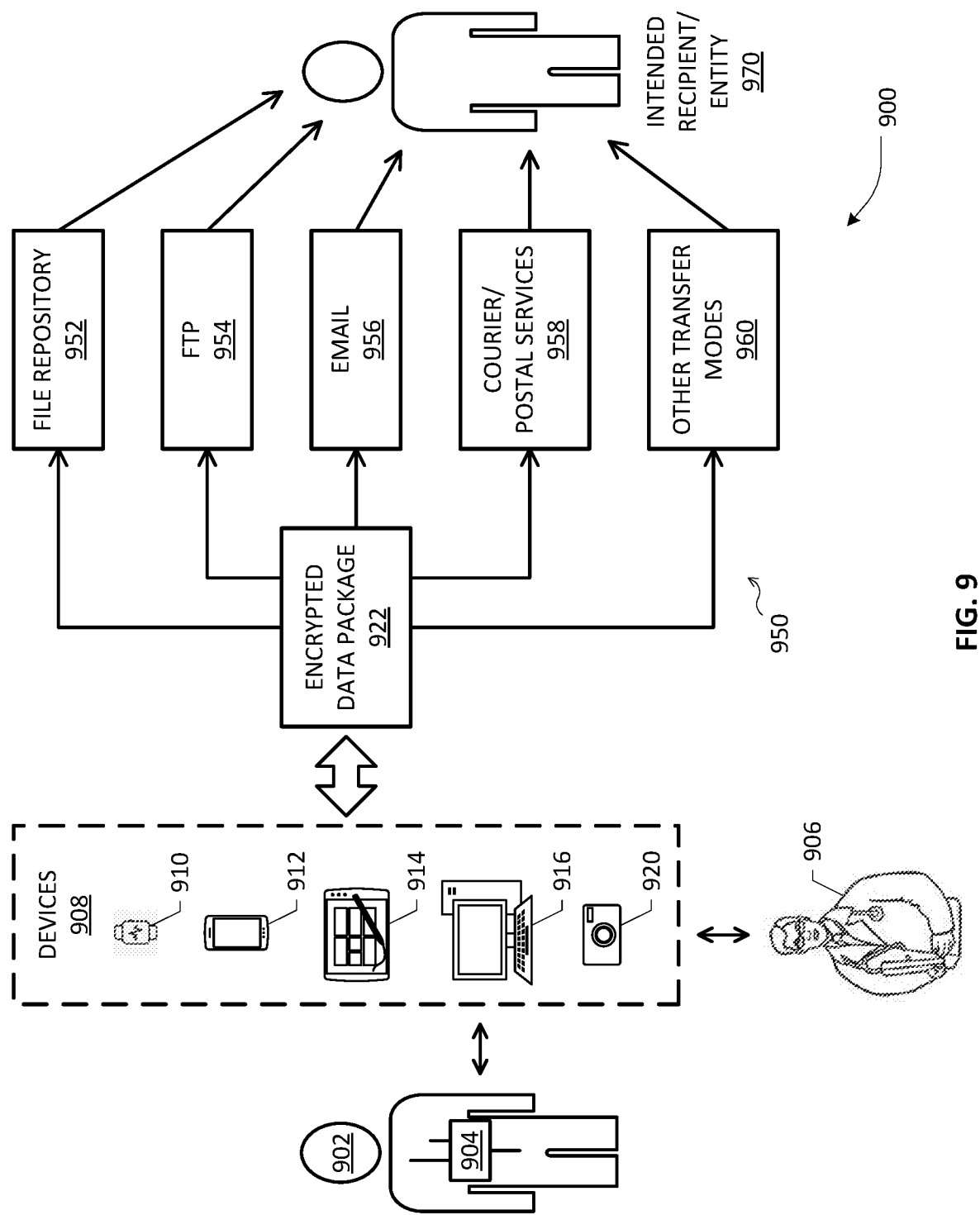
FIG. 9 depicts an example system or architecture for facilitating secure transfer of a patient data file according to an embodiment of the present patent disclosure.

FIG. 9 depicts an example system or architecture 900 for facilitating secure transfer of a patient data file according to an embodiment of the present patent disclosure. One or more devices 908, e.g., comprising smart wearables 910, smartphones 912, laptops/tablets/phablets 914, computers 916 and other portable and/or proprietary personal handheld/medical devices 920, are operative as patient controllers associated with a patient 902 having one or more IMDs 904, or as clinician programmers associated with a clinician 906, or as delegated third-party devices associated with caregivers (not specifically shown in this FIG.), authorized to provide therapy to and/or monitoring of patient 902 mediated through one or more programmers/devices 908 and IMD(s) 904 pursuant to a therapy application. Example therapy applications may comprise, without limitation, an SCS therapy, a neuromuscular stimulation therapy, a dorsal root ganglion (DRG) stimulation therapy, a deep brain stimulation (DBS) therapy, a cochlear stimulation therapy, a sacral nerve stimulation (SNS) therapy, a drug delivery therapy, a cardiac pacemaker therapy, an implantable cardioverter-defibrillator (ICD) therapy, a cardiac rhythm management (CRM) therapy, an electrophysiology (EP) mapping and radio frequency (RF) ablation therapy, an electroconvulsive therapy (ECT), a repetitive transcranial magnetic stimulation (rTMS) therapy, a vagal nerve stimulation (VNS) therapy, and one or more physiological condition monitoring applications, among others. One or more secure data packages 922 may be generated using a tandem encryption process in accordance with the teachings herein, which may be transmitted to recipient(s) and/or entity(ties) 970 using a plurality of transfer modes 950, such as cloud/web file repositories, FTP services 954, email systems 956, as well as courier/postal services 958 for shipping physical storage media containing the secure data packages (e.g., DVDs, CD-ROMs, hard disk drives, magnetic tape drives, magneto-optical drives, Blu-ray discs, optical disc drives, persistent memory cards and sticks, flash drives, solid-state drives, etc.). Additional transfer modes 960 are also contemplated for transferring the secure data packages one or more recipients 970 in further embodiments.

Based on the foregoing Detailed Description, it will be appreciated that example embodiments provide a tamper-proofing system and method that allows for secure transfer of sensitive patient data to a variety of intended recipients regardless of a modality selected by the senders, be it patients, clinicians, or respective agents, who may exercise their choice in myriad ways. Disclosed embodiments advantageously provide confidentiality, integrity, and authenticity—key security parameters desired in a file transfer system—while ensuring scalability and minimizing the logistical burden for key management, as well as avoiding the negative consequences of provisioning hard-coded symmetric keys in a device. The disclosed file data transfer scheme remains cryptoanalytically robust regardless of the selected modality such that compliance with applicable healthcare and/or data privacy/protection regulations and standards can be maintained.

Although specific examples of symmetric and asymmetric cryptography systems have been particularly described, it should be understood that embodiments herein are not necessarily limited thereto and various other SCS/ACS schemes may be implemented in a suitable tandem encryption scheme according to the teachings of the present disclosure in additional and/or alternative embodiments. For example, alternative SCS schemes may comprise block cipher schemes or stream cipher schemes, such as DES (Data Encryption Standard), IDEA (International Data Encryption Algorithm), Blowfish, RC4 (Rivest Cipher 4), RC5 (Rivest Cipher 5), and RC6 (Rivest Cipher 6), wherein DES, IDEA, Blowfish, RC5 and RC6 are block ciphers and RC4 is a stream cipher. Further, different AES modes may also be implemented in additional and/or alternative embodiments as an SCS scheme. Example ACS schemes may comprise Diffie-Hellman, Elliptic Curve Cryptography (ECC), Digital Signature Algorithm (DSA), and El Gamal schemes. Likewise, different types of cryptographic hashing functions may be used in additional and/or alternative embodiments, including, e.g., digital fingerprints, checksums, etc., having varying digest lengths. Accordingly, a tandem encryption scheme may be advantageously configured for purposes of the present disclosure using a number of different permutations and combinations of example ACS/SCS schemes as set forth herein depending on the needs of a particular implementation.

In the above-description of various embodiments of the present disclosure, it is to be understood that the terminology used herein is for the purpose of describing particular embodiments only and is not intended to be limiting of the invention. Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of this specification and the relevant art and may not be interpreted in an idealized or overly formal sense expressly so defined herein.

At least some example embodiments are described herein with reference to one or more circuit diagrams/schematics, block diagrams and/or flowchart illustrations. It is understood that such diagrams and/or flowchart illustrations, and combinations of blocks in the block diagrams and/or flowchart illustrations, can be implemented by any appropriate circuitry configured to achieve the desired functionalities. Accordingly, example embodiments of the present disclosure may be embodied in hardware and/or in software (including firmware, resident software, micro-code, etc.) operating in conjunction with suitable processing units or microcontrollers, which may collectively be referred to as "circuitry," "a module" or variants thereof. An example processing unit or a module may include, by way of illustration, a general purpose processor, a special purpose processor, a conventional processor, a digital signal processor (DSP), a plurality of microprocessors, one or more microprocessors in association with a DSP core, a controller, a microcontroller, Application Specific Integrated Circuits (ASICs), Field Programmable Gate Array (FPGA) circuits, any other type of integrated circuit (IC), and/or a state machine, as well as programmable system devices (PSDs) employing system-on-chip (SoC) architectures that combine memory functions with programmable logic on a chip that is designed to work with a standard microcontroller. Example memory modules or storage circuitry may include volatile and/or non-volatile memories such as, e.g., random access memory (RAM), electrically erasable/programmable read-only memories (EEPROMs) or UV-EPROMS, one-time programmable (OTP) memories, Flash memories, static RAM (SRAM), etc.

Further, in at least some additional or alternative implementations, the functions/acts described in the blocks may occur out of the order shown in the flowcharts. For example, two blocks shown in succession may in fact be executed substantially concurrently or the blocks may sometimes be executed in the reverse order, depending upon the functionality/acts involved. Moreover, the functionality of a given block of the flowcharts and/or block diagrams may be separated into multiple blocks and/or the functionality of two or more blocks of the flowcharts and/or block diagrams may be at least partially integrated. Furthermore, although some of the diagrams include arrows on communication paths to show a primary direction of communication, it is to be understood that communication may occur in the opposite direction relative to the depicted arrows. Finally, other blocks may be added/inserted between the blocks that are illustrated.

It should therefore be clearly understood that the order or sequence of the acts, steps, functions, components or blocks illustrated in any of the flowcharts depicted in the drawing Figures of the present disclosure may be modified, altered, replaced, customized or otherwise rearranged within a particular flowchart, including deletion or omission of a particular act, step, function, component or block. Moreover, the acts, steps, functions, components or blocks illustrated in a particular flowchart may be inter-mixed or otherwise inter-arranged or rearranged with the acts, steps, functions, components or blocks illustrated in another flowchart in order to effectuate additional variations, modifications and configurations with respect to one or more processes for purposes of practicing the teachings of the present patent disclosure.

Although various embodiments have been shown and described in detail, the claims are not limited to any particular embodiment or example. None of the above Detailed Description should be read as implying that any particular component, element, step, act, or function is essential such that it must be included in the scope of the claims. Where the phrases such as "at least one of A and B" or phrases of similar import are recited, such a phrase should be understood to mean "only A, only B, or both A and B." Reference to an element in the singular is not intended to mean "one and only one" unless explicitly so stated, but rather "one or more." Moreover, the terms "first," "second," and "third," etc. employed in reference to elements or features are used merely as labels, and are not intended to impose numerical requirements, sequential ordering or relative degree of significance or importance on their objects. All structural and functional equivalents to the elements of the above-described embodiments that are known to those of ordinary skill in the art are expressly incorporated herein by reference and are intended to be encompassed by the present claims. Accordingly, those skilled in the art will recognize that the exemplary embodiments described herein can be practiced with various modifications and alterations within the spirit and scope of the claims appended below.

The invention claimed is:

1. A method of facilitating secure transfer of a patient data file from a source device to a recipient, the method comprising:
   obtaining, by the source device, a symmetric cryptography system (SCS) key and a starting initialization vector (IV);
   iteratively performing, by the source device as each line of the patient data file is generated during runtime, a set of operations comprising:
      encrypting a plaintext line of the patient data file with the SCS key to obtain a corresponding ciphertext line, wherein the starting IV is incremented for each line subsequent to a first line of the patient data file;
      appending the corresponding ciphertext line into an accumulated encrypted file;
      obtaining a message digest of the accumulated encrypted file;
      encrypting the message digest, the SCS key and the starting IV using a public key of the recipient to obtain an encrypted header, the public key of the recipient corresponding to a private key of the recipient as part of an asymmetric cryptography system (ACS); and
      associating the encrypted header with the accumulated encrypted file and storing the encrypted header and the accumulated encrypted file; and
   transmitting the encrypted header and associated accumulated encrypted file either together or separately in one or more transfer modes from the source device to a receiver device associated with the recipient as a secure data package that is tamper-resistant irrespective of the transfer modes;
   upon receiving the secure data package, at the receiver device, decrypting the encrypted header using the private key of the receiver device to obtain a decrypted message digest, a decrypted SCS key and a decrypted starting IV;
   hashing, by the receiver device, the accumulated encrypted file to obtain a calculated message digest;
   comparing, by the receiver device, the calculated message digest with the decrypted message digest to verify integrity of the accumulated encrypted file;
   responsive to determining that the calculated message digest matches the decrypted message digest, decrypting, by the receiver device, the accumulated encrypted file by each ciphertext line using the decrypted SCS key, wherein the decrypted starting IV is applied for decrypting a first encrypted line and incremented on a line-by-line basis to obtain corresponding plaintext lines; and
   assembling, by the receiver device, the plaintext lines into a complete decrypted patient data file.

2. The method as recited in claim 1, wherein the SCS key comprises a dynamically generated key having one of: a 128-bit key length conforming to Advanced Encryption Standard (AES-128); a 192-bit key length conforming to AES-192; and a 256-bit key length conforming to AES-256.

3. The method as recited in claim 2, wherein the starting IV is dynamically generated and comprises a k-bit length corresponding to the SCS key, and further wherein the starting IV is applied for encrypting the first line and iteratively incremented by 1 for encrypting each subsequent line of the patient data file.

4. The method as recited in claim 3, wherein the encrypting a plaintext line comprises applying AES in a cipher block chaining (CBC) mode in combination with an integer counter (CTR) mode.

5. The method as recited in claim 4, wherein the obtaining a message digest of the accumulated encrypted file comprises applying a cryptographic hash function according to Secure Hash Algorithm (SHA) configured to provide a digest length of 256 bits.

6. The method as recited in claim 5, wherein the asymmetric cryptography system comprises a Rivest-Shamir-Adleman (RSA) public key cryptography system and further wherein a header containing the message digest, the AES key and the starting IV is padded to a length that matches a key modulus of the public key for generating the encrypted header.

7. A non-transitory computer-readable medium storing instructions that, when executed by one or more processors, cause the one or more processors to perform operations for facilitating secure transfer of a patient data file to a recipient, the operations comprising:
obtaining, by a source device, a symmetric cryptography system (SCS) key and a starting initialization vector (IV);
iteratively performing, by the source device as each line of the patient data file is generated during runtime, a set of operations comprising:
encrypting a plaintext line of the patient data file with the SCS key to obtain a corresponding ciphertext line, wherein the starting IV is incremented for each line subsequent to a first line of the patient data file;
appending the corresponding ciphertext line into an accumulated encrypted file;
obtaining a message digest of the accumulated encrypted file;
encrypting the message digest, the SCS key and the starting IV using a public key of the recipient to obtain an encrypted header, the public key of the recipient corresponding to a private key of the recipient as part of an asymmetric cryptography system (ACS); and
associating the encrypted header with the accumulated encrypted file and storing the encrypted header and the accumulated encrypted file; and
transmitting the encrypted header and associated accumulated encrypted file either together or separately in one or more transfer modes from the source device to a receiver device associated with the recipient as a secure data package that is tamper-resistant irrespective of the one or more transfer modes;
upon receiving the secure data package, at the receiver device, decrypting the encrypted header using the private key of the receiver device to obtain a decrypted message digest, a decrypted SCS key and a decrypted starting IV;
hashing, by the receiver device, the accumulated encrypted file to obtain a calculated message digest;
comparing, by the receiver device, the calculated message digest with the decrypted message digest to verify integrity of the accumulated encrypted file;
responsive to determining that the calculated message digest matches the decrypted message digest, decrypting, by the receiver device, the accumulated encrypted file by each ciphertext line using the decrypted SCS key, wherein the decrypted starting IV is applied for decrypting a first encrypted line and incremented on a line-by-line basis to obtain corresponding plaintext lines; and
assembling, by the receiver device, the plaintext lines into a complete decrypted patient data file.

8. The non-transitory computer-readable medium as recited in claim 7, wherein the SCS key comprises a dynamically generated key having one of: a 128-bit key length conforming to Advanced Encryption Standard (AES-128); a 192-bit key length conforming to AES-192; and a 256-bit key length conforming to AES-256.

9. The non-transitory computer-readable medium as recited in claim 8, wherein the starting IV is dynamically generated and comprises a k-bit length corresponding to the SCS key, and further wherein the starting IV is applied for encrypting the first line and iteratively incremented by 1 for each subsequent line of the patient data file.

10. The non-transitory computer-readable medium as recited in claim 9, wherein the operations for encrypting a plaintext line comprise applying AES in a cipher block chaining (CBC) mode in combination with an integer counter (CTR) mode.

11. The non-transitory computer-readable medium apparatus as recited in claim 10, wherein the operations for obtaining a message digest of the accumulated encrypted file comprise applying a cryptographic hash function according to Secure Hash Algorithm (SHA) configured to provide a digest length of 256 bits.

12. The non-transitory computer-readable medium as recited in claim 11, wherein the asymmetric cryptography system comprises a Rivest-Shamir-Adleman (RSA) public key cryptography system, and the operations further comprise padding a header containing the message digest, the AES key and the starting IV is padded to a length that matches a key modulus of the public key for generating the encrypted header.

13. A system for facilitating secure transfer of a patient data file to a recipient, the system comprising:
a sender device configured to:
generate a secure data package including an encrypted patient data file that is encrypted on a line-by-line basis using a symmetric cryptography system (SCS) having an SCS key and a starting initialization vector (IV), wherein a plaintext line of the patient data file is encrypted with the SCS key to obtain a corresponding ciphertext line and wherein the starting IV is incremented for each line subsequent to a first line of the patient data file, the secure data package further including an encrypted header containing a message digest of the encrypted patient data file, the SCS key and the starting (IV), the encrypted header obtained by applying a public key of a public key cryptography infrastructure associated with the recipient; and
transmit the secure data package in one or more transfer modes, wherein the secure data package is tamper-resistant irrespective of the one or more transfer modes; and
a receiver device associated with the recipient and configured to:
receive the secure data package in the one or more transfer modes;
decrypt the encrypted header of the secure data package using a private key of the recipient to obtain a decrypted message digest, a decrypted SCS key and a decrypted starting IV;
hash the encrypted patient data file to obtain a calculated message digest;
compare the calculated message digest with the decrypted message digest to verify integrity of the encrypted patient data file;
responsive to determining that the calculated message digest matches the decrypted message digest, decrypt the encrypted patient data file by each ciphertext line using the decrypted SCS key, wherein the decrypted starting IV is applied for decrypting a first ciphertext line and incremented on a line-by-line basis to obtain corresponding plaintext lines; and assemble the plaintext lines into a complete decrypted patient data file.

14. The system as recited in claim 13, wherein the SCS key comprises a dynamically generated key having one of: a 128-bit key length conforming to Advanced Encryption Standard (AES-128); a 192-bit key length conforming to AES-192; and a 256-bit key length conforming to AES-256.

15. The system as recited in claim 14, wherein the starting IV is dynamically generated and comprises a k-bit length corresponding to the SCS key, and further wherein the starting IV is applied for encrypting the first line and iteratively incremented by 1 for each subsequent line of the patient data file.

16. The system as recited in claim 15, wherein each plaintext line is encrypted using AES in a cipher block chaining (CBC) mode in combination with an integer counter (CTR) mode.

17. The system as recited in claim 16, wherein the message digest is obtained by a cryptographic hash function according to Secure Hash Algorithm (SHA) configured to provide a digest length of 256 bits.

18. The system as recited in claim 17, wherein the public key cryptography infrastructure comprises a Rivest-Shamir-Adleman (RSA) public key cryptography system, and further wherein a header containing the message digest, the AES key and the starting IV is padded to a length that matches a key modulus of the public key for generating the encrypted header.

19. The system as recited in claim 18, wherein the sender device comprises at least one of a patient controller device, a clinician controller device, and a personal medical device of a patient.

\* \* \* \* \*

UNITED STATES PATENT AND TRADEMARK OFFICE
CERTIFICATE OF CORRECTION

| | |
|---|---|
| PATENT NO. | : 11,582,022 B1 |
| APPLICATION NO. | : 17/088287 |
| DATED | : February 14, 2023 |
| INVENTOR(S) | : Creek et al. |

It is certified that error appears in the above-identified patent and that said Letters Patent is hereby corrected as shown below:

In the Claims

At Column 20, Claim number 11, starting at Line number 12, delete "computer-readable medium apparatus" and replace with --computer-readable medium--.

Signed and Sealed this
Fourth Day of April, 2023

*Katherine Kelly Vidal*
Katherine Kelly Vidal
*Director of the United States Patent and Trademark Office*